(12) United States Patent
Shine

(10) Patent No.: US 6,440,089 B1
(45) Date of Patent: Aug. 27, 2002

(54) UTERINE CONTRACTION DETECTOR AND FREQUENCY TRENDER

(75) Inventor: David J. Shine, Hamden, CT (US)

(73) Assignee: GE Medical Systems Information Technologies, Inc., Waukesha, WI (US)

( * ) Notice: Subject to any disclaimer, the term of this patent is extended or adjusted under 35 U.S.C. 154(b) by 19 days.

(21) Appl. No.: 09/590,036

(22) Filed: Jun. 7, 2000

(51) Int. Cl.⁷ ............................................... A61B 5/103
(52) U.S. Cl. ...................................................... 600/591
(58) Field of Search ................................ 600/551, 588, 600/516, 304, 591

(56) References Cited

U.S. PATENT DOCUMENTS

| | | | | |
|---|---|---|---|---|
| 3,989,034 A | | 11/1976 | Hojaiban | |
| 4,967,761 A | * | 11/1990 | Nathanielsz | 600/546 |
| 5,042,503 A | * | 8/1991 | Torok et al. | 600/588 |
| 5,070,888 A | * | 12/1991 | Hon et al. | 600/588 |
| 5,217,022 A | * | 6/1993 | Nathanielsz | 600/546 |
| 5,471,993 A | * | 12/1995 | Yoches et al. | 600/588 |
| 5,785,664 A | * | 7/1998 | Rosenberg | 600/588 |
| 5,871,499 A | * | 2/1999 | Hahn et al. | 606/202 |

\* cited by examiner

*Primary Examiner*—Kevin Shaver
*Assistant Examiner*—Pamela L. Wingood
(74) *Attorney, Agent, or Firm*—Michael Best & Friedrich LLP

(57) ABSTRACT

A method and apparatus for detecting uterine contractions, determining the frequency of uterine contractions, trending the frequency data, and generating a real time graphical representation of the determined frequency. The invention employs commonly known methods of uterine activity detection. The uterine activity data is analyzed to determine the occurrence and frequency of contractions. The determined frequency of multiple time periods is displayed on a maternal/fetal monitor in real time over the course of labor.

48 Claims, 5 Drawing Sheets

UTERINE CONTRACTION DETECTOR AND FREQUENCY TRENDER

BACKGROUND OF THE INVENTION

This invention relates to a fetal monitoring device, and particularly to a fetal monitor that detects uterine contractions, determines the frequency of uterine contractions, and generates a real time graphical representation of the determined frequency.

A tocodynamometer or a uterine pressure catheter is commonly used to collect uterine activity or contraction data. These devices are pressure sensors or force transducers that monitor uterine activity by mechanically sensing the pressure caused by the uterine contraction.

In the case of a tocodynamometer, the transducer is attached to a belt that is strapped to the mother's abdomen. During a uterine contraction, the transducer is pressed between the abdomen and the belt and a contraction is registered. In the case of an intrauterine pressure catheter, an intrauterine pressure sensor is inserted by catheter through the birth canal and into the uterus. The sensor registers the change in uterine pressure that occurs during a contraction.

The contractions are also referred to as uterine activity and the indication of such activity by the tocodynamometer or the intrauterine pressure sensor is called uterine activity data. The uterine activity data is sampled by the fetal monitor and plotted over time on a strip chart. Uterine contractions appear as humps in the waveform shown on the strip chart. Typically, a clinician visually inspects the strip chart and counts the humps to identify the frequency of uterine contractions over a given period of time, usually ten minutes.

This method of determining the frequency of uterine contractions is time consuming. The frequency of contractions is essential information in determining the progress of labor. Each time the progress of labor needs to be determined, a clinician must take the time to visually inspect the strip chart to determine the frequency of contractions. A clinician must manually record each frequency determination to compare the frequency of contractions for the current time period with previous time periods. Thus, a clinician must continually visually inspect a long strip chart to make simple assessments for determining the progress of labor.

SUMMARY OF THE INVENTION

Accordingly, the invention provides a method and apparatus for detecting uterine contractions, determining the frequency of uterine contractions, and generating a real time graphical representation of the determined frequency. Rather than using the manually recorded frequency of contractions from the strip chart, the real time graphical representation can be used to easily monitor the progress of labor. The physical representation shows the determined frequency for each time period in an easy to read format allowing for comparison between multiple time periods. A clinician can efficiently and accurately determine the progress of labor by comparing the frequency of contractions in multiple time periods.

The invention employs commonly known methods of uterine activity detection, including, but not limited to, tocodynamometers and intrauterine pressure catheters. Once the uterine activity data is gathered, a maternal/fetal monitor analyzes the data. The maternal/fetal monitor determines the occurrence and frequency of contractions. The maternal/fetal monitor trends the uterine contraction frequency data over the course of labor and generates a graphical representation of the data. The maternal/fetal monitor displays the graphical representation in the form of a time-frequency graph with a bar for every time period to indicate the number of contractions for that time period. Multiple time periods over the course of labor are displayed in real time on the maternal/fetal monitor.

The invention further includes a method of detecting and displaying uterine contraction frequency. The method includes detecting uterine contractions from uterine activity data, determining the frequency of contractions, and generating a graphical display of the frequency of contractions over real time.

The invention further includes a software program for analyzing uterine activity data. The software program determines the occurrence and frequency of contractions. The software program then generates a graphical display of the frequency of contractions over real time.

It is an advantage of the invention to eliminate the need to visually inspect a strip chart to determine the occurrence and frequency of uterine contractions.

It is another advantage of the invention to eliminate the need to manually record the determined frequency of uterine contractions in order to monitor the progress of labor.

It is still another advantage of the invention to provide an efficient and accurate method of determining and displaying the frequency of uterine contractions over real time.

Various other features and advantages of the invention are set forth in the following drawings, detailed description, and claims.

DETAILED DESCRIPTION OF THE PREFERRED EMBODIMENT

Figure 1:
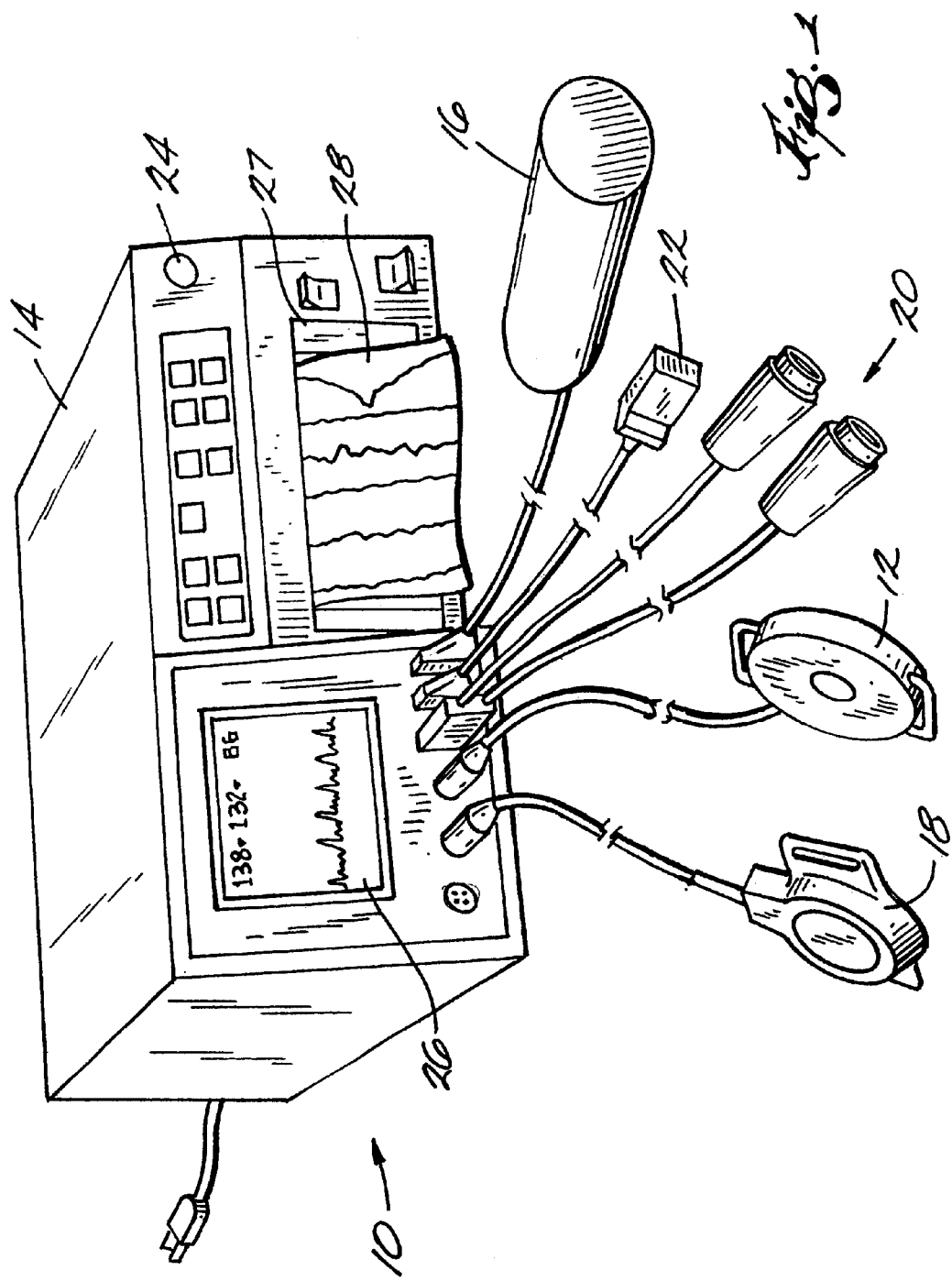
FIG. 1 is a perspective view of a maternal/fetal monitor embodying the invention.

Before one embodiment of the invention is explained in detail, it is to be understood that the invention is not limited in its application to the details of construction and the arrangements of the components set forth in the following description or illustrated in the drawings. The invention is capable of other embodiments and of being practiced or being carried out in various ways. Also, it is understood that the phraseology and terminology used herein is for the purpose of description and should not be regarded as limiting. The use of "including" and "comprising" and variations thereof herein is meant to encompass the items listed thereafter and equivalents thereof as well as additional items.

Shown in FIG. 1 is a maternal/fetal monitor 10 embodying the invention. Maternal/fetal monitor 10 includes a uterine activity sensor 12 for detecting or acquiring uterine activity data, and an analysis module 14 for determining the frequency of uterine contractions from the detected uterine activity data and for generating a time-frequency representation of the frequency of the uterine contractions.

Uterine activity sensor 12 may be any well-known uterine activity-sensing device. In FIG. 1, uterine activity sensor 12 is shown as a tocodynamometer. A tocodynamometer is a transducer attached to a belt that is strapped to the mother's abdomen. Once the tocodynamometer belt is strapped to the mother's abdomen, the clinician pushes a button on maternal/fetal monitor 10 to set a baseline for the algorithm used by analysis module 14. The transducer records relative changes from the baseline in abdominal tension caused by uterine contractions. Thus, the transducer gathers uterine activity data.

Uterine activity sensor 12 may also be an intrauterine pressure catheter (not shown). An intrauterine pressure catheter is inserted transcervically into the uterine cavity to measure intrauterine pressure. The catheter may be a fluid-filled catheter or a transducer-tipped catheter. Once the intrauterine pressure catheter is positioned in the uterine cavity, the clinician pushes a button on maternal/fetal monitor 10 to set a baseline for the algorithm used by analysis module 14. The catheter records relative changes in intrauterine pressure from the baseline caused by uterine contractions. Thus, the catheter gathers uterine activity data.

Maternal/fetal monitor 10 is also connected to a noninvasive blood pressure measuring device 16, an ultrasonic sensor 18, fetal and maternal ECG sensors 20, and fetal and maternal pulse oximetry sensors 22. These sensors are all conventional and need not be discussed in detail for. purposes of understanding the present invention. Maternal/fetal monitor 10 also includes a trim knob 24 to be used similar to a personal computer mouse to access softkeys on a graphical display 26. Maternal/fetal monitor 10 includes a conventional strip chart recorder 27 to display data in the form of continuous waveforms on a paper strip chart 28.

Figure 2:
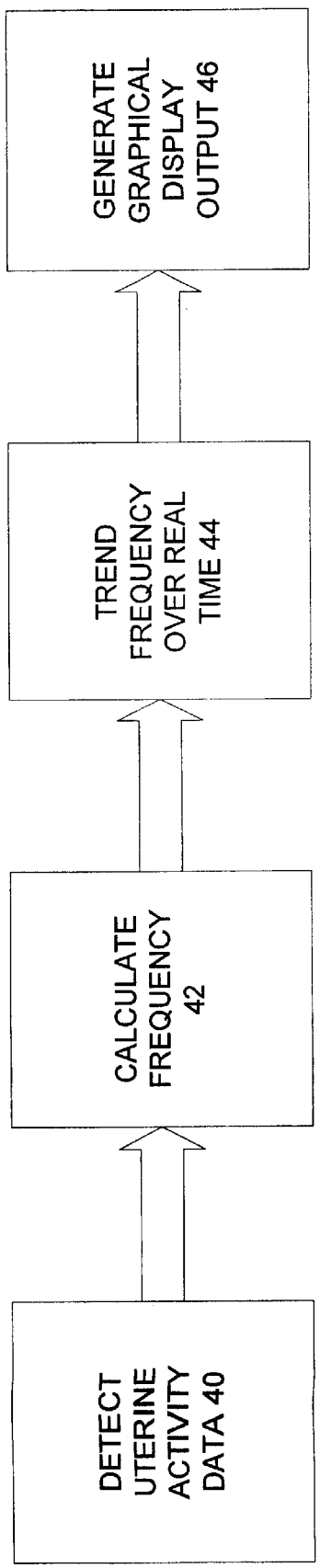
FIG. 2 is a flowchart illustrating the method of the invention.

FIG. 2 is a block diagram illustrating the method of the invention. Uterine activity sensor 12 detects uterine activity data 40. The uterine activity data is received by analysis module 14 of maternal/fetal monitor 10. The analysis module 14 uses an algorithm to calculate the frequency of uterine contractions for a given period of time 42, trends the frequency over time 44, and then generates 46 a time-frequency graphical output and a uterine activity value on display 26. In the preferred embodiment, the acts of calculating the frequency 42, trending the frequency 44, and generating a display 46 are performed using a software-based program which is either installed into an existing maternal/fetal monitor or is installed in a computer adapted to receive uterine activity data from an external source.

Figure 3:
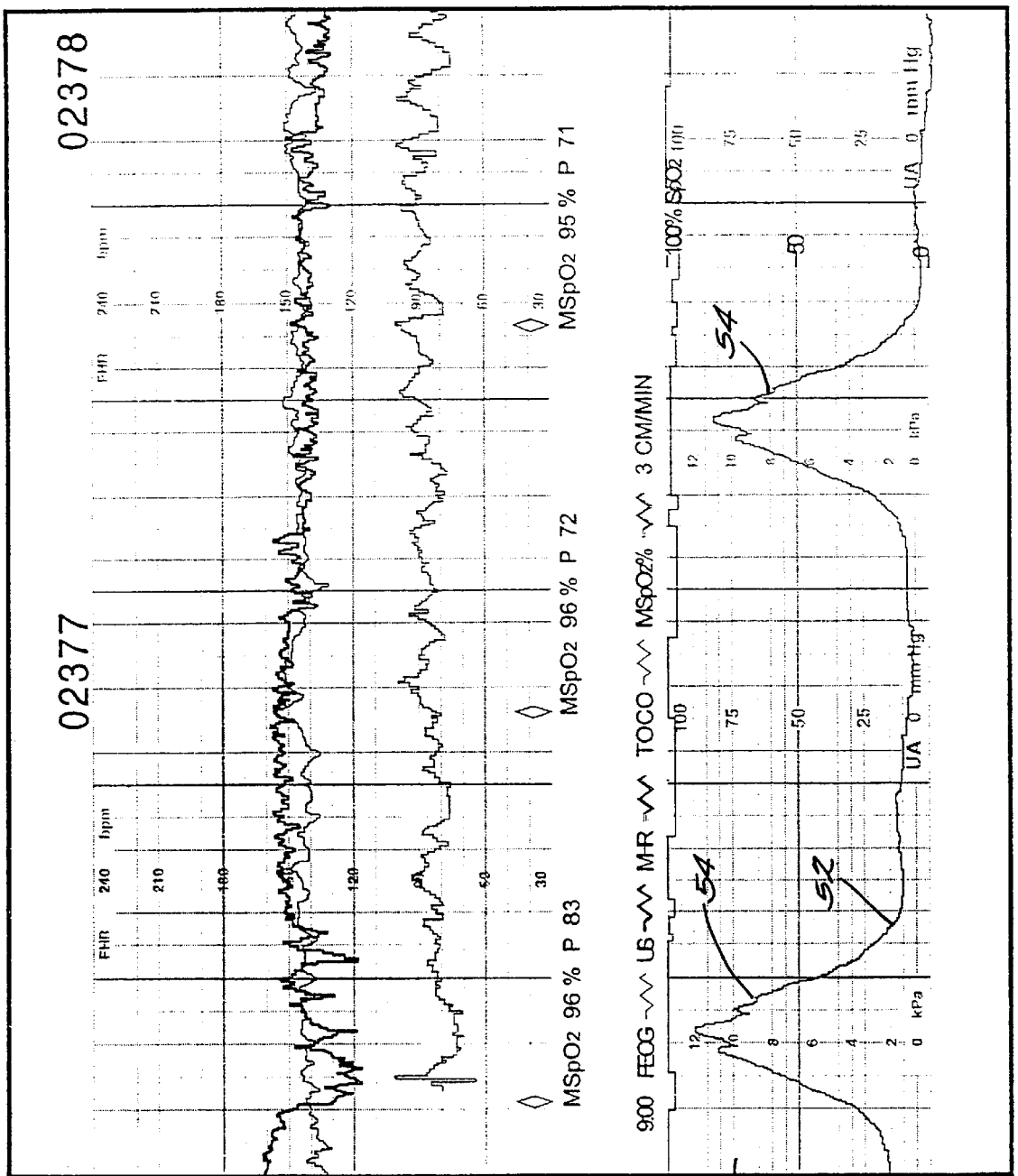
FIG. 3 is a typical strip chart including the uterine activity data waveform.

FIG. 3 illustrates a typical paper strip chart 28 of maternal/fetal monitor 10. The lower portion 50 of the graphical output in FIG. 3 includes a uterine activity data waveform 52 representing uterine activity data gathered by the tocodynamometer or the intrauterine pressure catheter. Humps 54 in the uterine activity data waveform 52 represent uterine contractions. The uterine activity data gathered by either the tocodynamometer or the intrauterine pressure catheter is sent as input data to analysis module 14.

The occurrence and frequency of contractions may be calculated by analysis module 14 in any well-known manner. In the embodiment shown in the drawings, the analysis module 14 detects the occurrence of contractions by using an algorithm to calculate the change in incremental slope of the uterine activity data waveform 52 over time. One such algorithm is disclosed in U.S. Pat. No. 3,989,034 which is incorporated herein by reference. The algorithm preferably calculates the incremental slope of the uterine activity data waveform 52 in real time. Once the incremental slope rises sufficiently from a stable baseline such that it meets contraction onset criteria, the onset of a contraction is registered. As the incremental slope then declines sufficiently such that it meets contraction offset criteria, and then stabilizes at a baseline, the event will be qualified as a completed contraction and recorded by a counter. In other embodiments (not shown), the onset and offset incremental slope criteria may vary and may not be equal, but would affect a similar waveform pattern recognition methodology. The frequency of contractions is determined by counting the number of contraction occurrences that are registered in the counter in a given time period.

In the preferred embodiment, the number of contraction occurrences is measured in ten-minute time periods. The frequency of contractions is then displayed as uterine contractions per ten minutes (UC/10). In another preferred embodiment, the time period for measuring the frequency is variable and may be set by the clinician.

In other embodiments, analysis module 14 determines the frequency of contractions using an incremental area method. In the incremental area method, the baseline can be set under or over the uterine activity waveform, and the algorithm calculates the incremental area under or over the uterine activity data waveform 52. Once the incremental area between the baseline and the waveform rises to a predetermined value, the occurrence of a contraction is registered in the counter in analysis module 14. The frequency of contractions is determined by counting the number of contraction occurrences that are registered in the counter in a given time period. In yet another embodiment, the elements of both the running slope evaluation method and the area under the curve method are combined.

Analysis module 14 generates a time-frequency representation of the uterine contraction frequency data. Analysis module 14 trends the uterine contraction frequency data in real time over the course of labor and creates a graphical output of the uterine contraction frequency data. The real time graphical output is displayed on display 26 of maternal/fetal monitor 10 at the request of the clinician.

Figure 4:
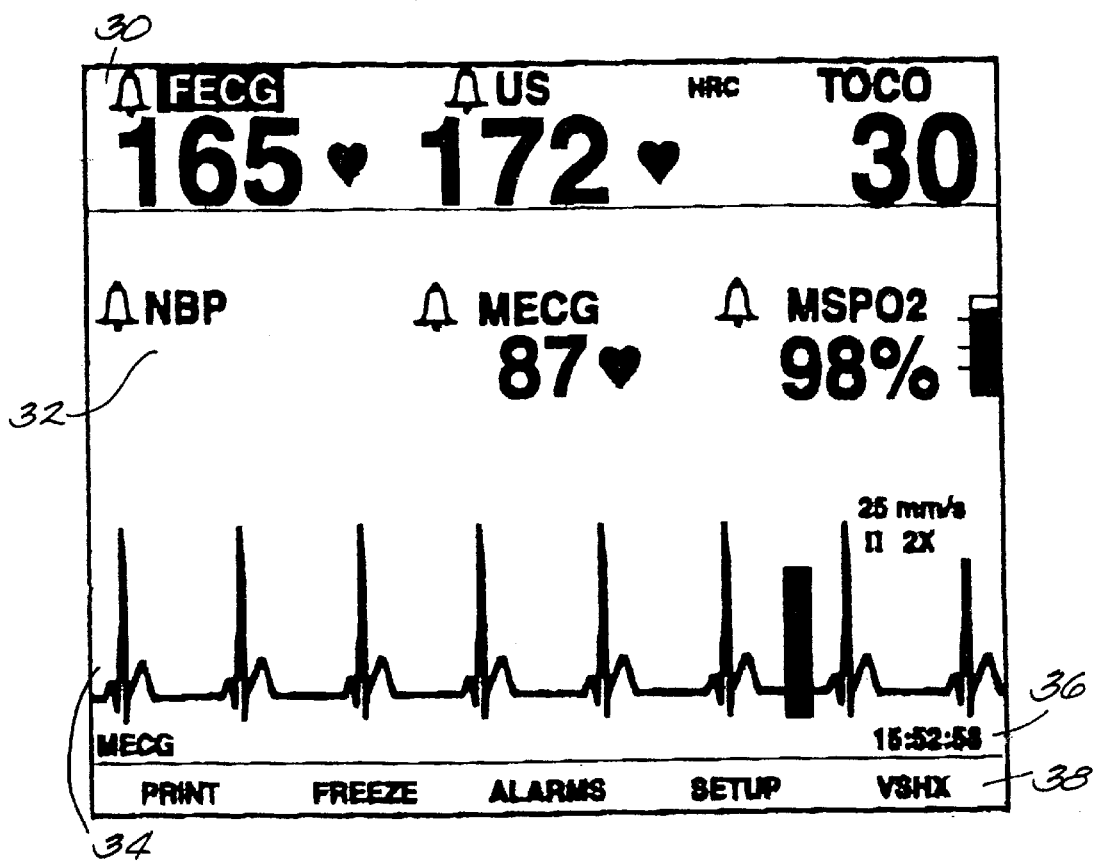
FIG. 4 is typical maternal/fetal monitor display screen.
Figure 5:
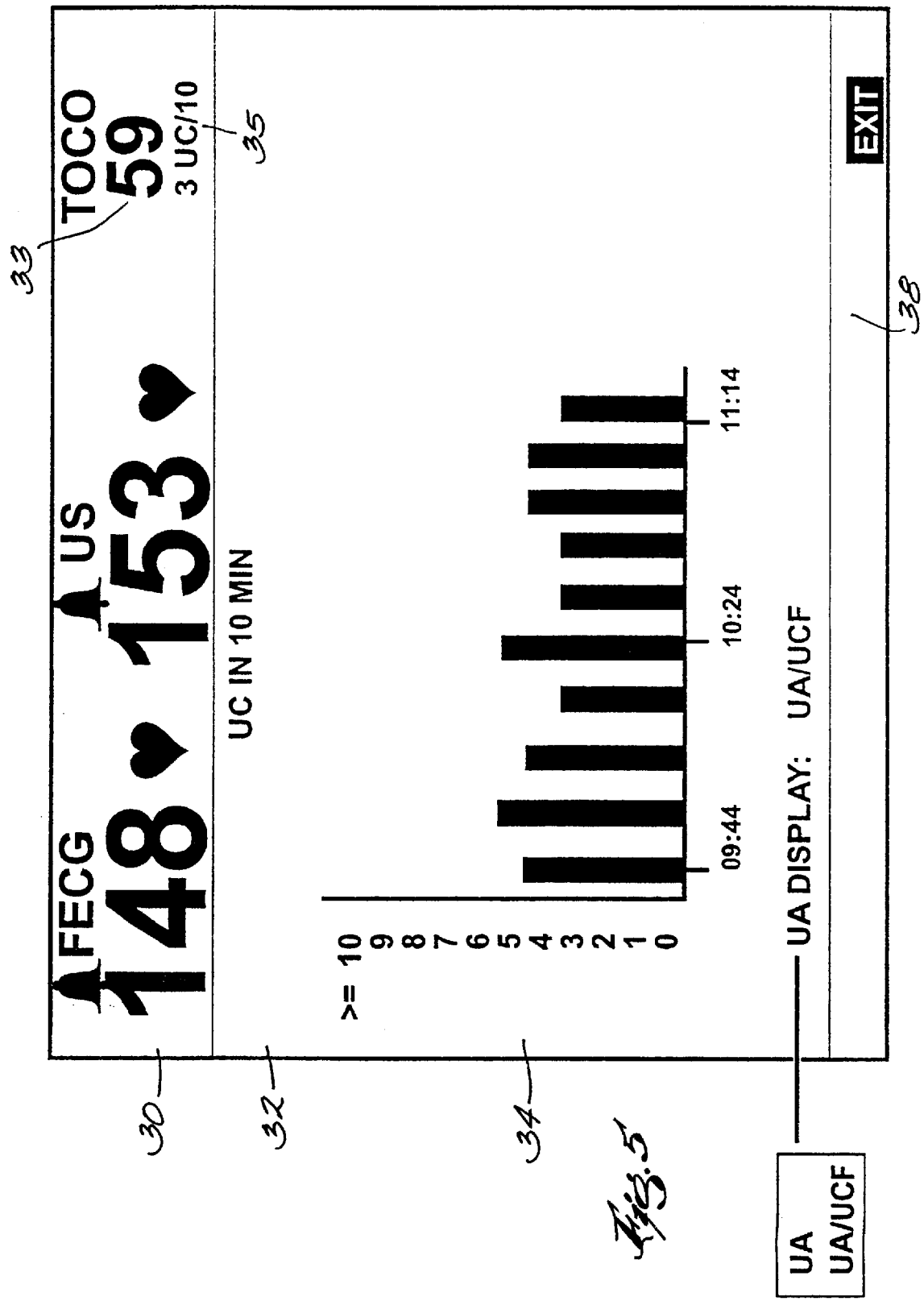
FIG. 5 is a maternal/fetal monitor display screen with the uterine contraction frequency data represented by a histogram.

As illustrated in FIG. 4, display 26 is divided into five horizontal sections. A primary labor parameters area 30 displays one or more of the following parameters: ultrasound data, fetal ECG, and uterine activity. An additional parameters area 32 displays one or more of the following parameters: maternal blood pressure, maternal heart rate and maternal pulse oximetry. A waveform area 34 displays one of the following waveforms: fetal ECG, maternal ECG or maternal pulse oximetry. A time area 36 displays the current time. A softkey area 38 displays softkeys for system configuration. To access the uterine contraction frequency waveform, the clinician rotates trim knob 24 to highlight a corresponding softkey located, as mode label, above UA value in area 30. The clinician then presses trim knob 24 to select the corresponding softkey and to display the uterine contraction frequency graphical output in area 32 and 34 as shown in FIG. 5. Trim knob 24 and softkey area 38 allow the clinician to tailor the appearance of or presentation of information on display 26 of maternal/fetal monitor 10 for each individual patient.

In the preferred embodiment, the uterine contraction frequency graphical output is displayed in area 32 and 34 as a histogram. As shown in FIG. 5, the histogram includes bars representing the number of uterine contractions in a ten-minute time period. A series of ten bars is displayed in real time representing 100 minutes of uterine contraction frequency data. The histogram changes over real time in order to display the most recent 100 minutes of uterine contraction frequency data. As shown in FIG. 5, maternal/fetal monitor 10 also displays the current uterine contraction frequency value 35 in units of UC/10 below the uterine pressure value 33 in primary labor parameter area 30. In another preferred embodiment, the number of bars displayed in the histogram is variable and may be set by the clinician. In yet another embodiment, the clinician may change frequency units from UC/10 to a difference value which meets their protocol (ex. UC/15, UC/20).

Various features and advantages of the invention are set forth in the following claims.

What is claimed is:

1. A monitoring device comprising:
   a sensor for acquiring uterine activity data; and
   an analysis module for determining the frequency of uterine contractions from the detected uterine activity data and for generating a time-frequency representation of the frequency of the uterine contractions.

2. The device in claim 1 wherein the sensor for acquiring uterine activity data is a tocodynamometer.

3. The device in claim 1 wherein the sensor for acquiring uterine activity data is a intrauterine pressure catheter.

4. The device in claim 1 wherein the uterine activity data is represented by a waveform and the analysis module identifies uterine contractions using a waveform pattern recognition method that calculates the change in incremental slope over time of the waveform of the detected uterine activity.

5. The device in claim 4 wherein each contraction identified is counted and the count is converted to a frequency.

6. The device in claim 1 wherein the uterine activity data is represented by a waveform and wherein the analysis module identifies uterine contractions using a waveform pattern recognition method that calculates the change over time in the incremental area under or over the waveform of the detected uterine activity.

7. The device in claim 6 wherein each contraction identified is counted and the count is converted to a frequency.

8. The device in claim 1 wherein the analysis module generates the time-frequency representation in real time over the course of labor.

9. The device in claim 1 wherein the analysis module generates the time-frequency representation in the form of a histogram.

10. The device in claim 1 wherein the analysis module determines the frequency of uterine contractions for variable time periods.

11. The device in claim 1 wherein the analysis module determines the frequency of uterine contractions for 10 minute time periods.

12. The device in claim 11 wherein the analysis module determines 10 time periods for a total of 100 minutes of frequency data.

13. A method of detecting and displaying uterine activity data, the method comprising the acts of:
   acquiring uterine activity data;
   determining the frequency of uterine contractions from the detected uterine activity data over a selected period of time; and
   generating a time-frequency representation of the frequency of the uterine contractions.

14. The method in claim 13 and further comprising the act of detecting uterine activity using a tocodynamometer.

15. The method in claim 13 and further comprising the act of detecting uterine activity using an intrauterine pressure catheter.

16. The method in claim 13 wherein the uterine activity data is represented by a waveform and wherein the uterine contractions are identified using a waveform pattern recognition method that calculates the change in incremental slope over time of the waveform.

17. The method in claim 16 and further comprising the acts of counting the uterine contractions and converting the count to a frequency.

18. The method in claim 13 wherein the uterine activity data is represented by a waveform and wherein the uterine contractions are identified using a waveform pattern recognition method that calculates the change over time in the incremental area under or over the waveform.

19. The method in claim 18 and further comprising the acts of counting the uterine contractions and converting the count to a frequency.

20. The method in claim 13 wherein the time-frequency representation is generated in real time over the course of labor.

21. The method in claim 13 wherein the time-frequency representation is in the form of a histogram.

22. The method in claim 13 wherein the given period of time for which the frequency of uterine contractions is variable.

23. The method in claim 13 wherein the frequency of uterine contractions is determined for 10 minute time periods.

24. The method in claim 23 wherein 10 time periods are displayed for a total of 100 minutes of frequency data.

25. A monitoring device comprising:
   a uterine activity detector;
   a uterine contraction detection algorithm for determining the frequency of the detected uterine contractions over a selected period of time; and
   a display device for providing a user readable representation of the frequency of detected uterine contractions.

26. The device in claim 25 wherein the uterine activity detector is a tocodynamometer.

27. The device in claim 25 wherein the uterine activity detector is an intrauterine pressure catheter.

28. The device in claim 25 wherein the uterine activity data is represented by a waveform and the uterine contractions are identified using waveform pattern recognition software that calculates the change in incremental slope over time of the waveform of the detected uterine activity.

29. The device in claim 28 wherein each identified contraction is counted and the count is converted to a frequency.

30. The device in claim 25 wherein the uterine activity data is represented by a waveform and the uterine contractions are identified using waveform pattern recognition software that calculates the change over time in the incremental area under or over the waveform of the detected uterine activity.

31. The device in claim 30 wherein each identified contraction is counted and the count is converted to a frequency.

32. The device in claim 25 wherein the time-frequency representation is displayed in real time over the course of labor.

33. The device in claim 25 wherein the time-frequency representation is in the form of a histogram.

34. The device in claim 25 wherein the frequency of uterine contractions can be determined for variable time periods.

35. The device claim 25 wherein the frequency of uterine contractions is determined for 10 minute time periods.

36. The device in claim 35 wherein 10 time periods are displayed for a total of 100 minutes of frequency data.

37. A uterine activity frequency trending software system comprising:

a software-based data input module for receiving input data of uterine activity; and a software algorithm for determining the frequency of uterine contractions from the uterine activity data over a selected period of time and for generating output data of a time-frequency representation of the uterine contractions.

38. The system in claim 37 wherein the input module receives input data from a tocodynanometer.

39. The system in claim 37 wherein the input module receives input data from a intrauterine pressure catheter.

40. The system in claim 37 wherein the uterine activity data is represented by a waveform and the software algorithm identifies the uterine contractions by calculating the change in incremental slope over time of the waveform of the detected uterine activity.

41. The system in claim 40 wherein each identified contraction is counted and wherein the count is converted to a frequency.

42. The system in claim 37 wherein the uterine activity data is represented by a waveform and the software algorithm identifies uterine contractions by calculating the change over time in the incremental area under or over the waveform of the detected uterine activity.

43. The system in claim 42 wherein each identified contraction is counted and wherein the count is converted to a frequency.

44. The system in claim 37 wherein the software algorithm generates output data of the time-frequency representation in real time over the course of labor.

45. The system in claim 37 wherein the software algorithm generates output data of the time-frequency representation in the form of a histogram.

46. The system in claim 37 wherein the software algorithm determines the frequency of uterine contractions for variable time periods.

47. The system in claim 37 wherein the software algorithm determines the frequency of uterine contractions for 10 minute time periods.

48. The system in claim 47 wherein the software algorithm determines the frequency of uterine contractions for 10 time periods for a total of 100 minutes of frequency data.

* * * * *